(12) United States Patent  
Arquette

(10) Patent No.: US 7,097,866 B2  
(45) Date of Patent: *Aug. 29, 2006

(54) COMPOSITION AND METHOD TO WHITEN AND EXFOLIATE SKIN

(75) Inventor: James Demetrios G. Arquette, Tempe, AZ (US)

(73) Assignee: Desert Whale Jojoba Company, Tucson, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 11/086,194

(22) Filed: Mar. 22, 2005

(65) Prior Publication Data

US 2005/0163733 A1   Jul. 28, 2005

Related U.S. Application Data

(62) Division of application No. 10/316,375, filed on Dec. 11, 2002, now Pat. No. 6,890,566.

(51) Int. Cl.  
*A01N 65/00* (2006.01)

(52) U.S. Cl. .................................................. 424/725

(58) Field of Classification Search ................. 424/725  
See application file for complete search history.

(56) References Cited

U.S. PATENT DOCUMENTS

2001/0012840 A1 * 8/2001 Verbiscar .................... 514/164  
2003/0133958 A1 * 7/2003 Kuno et al. .................. 424/401

* cited by examiner

*Primary Examiner*—Patricia Leith  
(74) *Attorney, Agent, or Firm*—Dale F Regelman

(57) ABSTRACT

A composition which is effective as a skin whitening agent is disclosed. The composition includes one or more jojoba plant parts. The composition further includes Simmondsin. A method of promoting skin whitening, comprising the step of topically administering to an individual a composition in an amount effective to whiten skin, where that composition comprises one or more parts of the jojoba plant.

11 Claims, 1 Drawing Sheet

US 7,097,866 B2

COMPOSITION AND METHOD TO WHITEN AND EXFOLIATE SKIN

CROSS-REFERENCE TO RELATED APPLICATIONS

This Application is a Divisional Application claiming priority to the Application having Ser. No. 10/316,375 filed Dec. 11, 2002 now U.S. Pat. No. 6,890,566.

FIELD OF THE INVENTION

Applicant's invention relates to a composition and method to whiten, and optionally exfoliate, skin.

BACKGROUND OF THE INVENTION

Exposure to the sun over time can induce many biochemical reactions in the skin. For example, exposure can lead to sunburn and tanning, which are immediate and well recognized. Other consequences of exposure to the sun are more subtle and accumulate over time. Often melanocytes can accumulate and the action of the enzyme tyrosinase is increased. These changes can result in the development of age spots and create an uneven, mottled skin tone. Unfortunately, many of the commercially available products in today's market are either only marginally effective, or contain active agents that are unstable and lose their potency when incorporated into a final formula.

The ability to modify the expression of pigment content in the skin, to promote an even-looking skin tone and a more youthful appearance, is highly desired in today's society. Many people desire to modify their skin tone, to reduce aging spots, melasma, etc., or for purely cosmetic reasons. In fact, in the Far East, a lighter skin tone is desirable and is associated with higher socio-economic status.

Hyper-pigmentation in the skin is caused by the over expression or accumulation of melanin in the skin. As a result, the pathway involved in melanin production has been the target for many inhibitors so as to reduce the levels produced. One of the principal enzymes involved in the melanin pathway is tyrosinase.

Skin functions include, inter alia, protection, heat regulation, immune response, and sensory detection. With age, the skin's natural rejuvenation process slows. In addition, skin aging many times results in development of not only hyperpigmentation, but also hyperkeratinization wherein comeocytes adhere in excess causing a thickening of the stratum corneum. The stratum corneum comprises a portion of the epidermis, and includes nonviable corneocytes which are cells that have lost the nucleus and cytoplasm organelles.

What is needed is a composition which can be effectively used as a topically applied skin whitening agent. In addition, it is desirable to have a topical composition which can whiten skin as well as induce shedding of dry scales from the skin's surface thereby promoting a rejuvenated, fresher complexion. Applicant has now discovered a composition comprising tyrosinase inhibitors, and/or melanin cell synthesis inhibitors, in optional combination with skin exfoliating agents, which is useful in topically applied cosmetic and pharmaceutical formulations.

SUMMARY OF THE INVENTION

Applicants' invention includes a composition which is effective as a skin whitening agent. Applicant's composition comprises jojoba. By "jojoba," Applicant means any portion of the jojoba plant, including without limitation jojoba meal, but not including jojoba oil. In certain embodiments, Applicant's composition comprises jojoba in combination with jojoba oil. Applicant's composition includes Simmondsin and/or Simmondsin derivatives. Applicant's invention further includes a method of promoting skin whitening, comprising the step of topically administering to an individual a composition in an amount effective to whiten skin, where that composition comprises jojoba.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Figure 1:
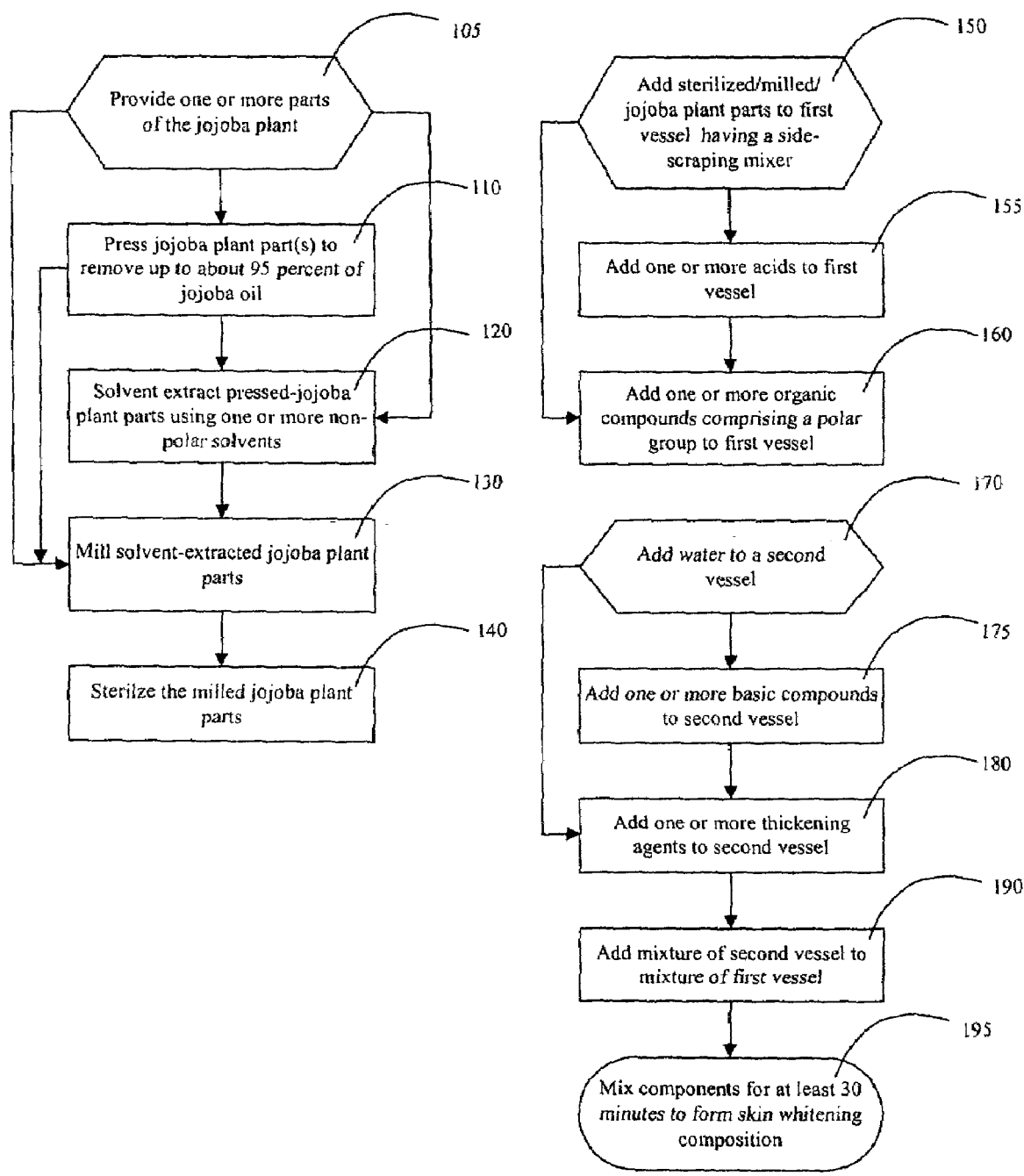
FIG. 1 is a flow chart summarizing the steps of Applicant's method to form his composition.

Referring to the illustrations, like numerals correspond to like parts depicted in the figures. The invention will be described as embodied in composition which includes jojoba meal. Applicant's invention, however, is not limited to use of jojoba meal. Rather, Applicant's invention includes a composition comprising one or more parts of the jojoba plant, including but not limited to jojoba seed, pressed jojoba seed, jojoba roots, jojoba bark, jojoba leaves, and combinations thereof. Applicant's invention further includes use of Applicant's composition to affect the visual appearance of skin.

All patents, applications, test methods and publications referenced in this specification are hereby incorporated by reference in their entirety. In case of conflict, the present description, including definitions, will prevail. The present invention is directed in part to a composition which is useful as a skin whitening agent. Specifically, the invention is directed in part to a composition comprising one or more jojoba plant parts. Applicant's composition includes Simmondsin and/or Simmondsin derivatives. In certain embodiments, Applicant's composition further comprises a plurality of proteins and peptide fragments which naturally occur in the jojoba plant. By "peptide fragments," Applicant means one or more amino acid oligomers derived from the cleavage of one or more jojoba proteins. In certain embodiments, Applicant's composition further includes a plurality of amino acids.

FIG. 1 summarizes Applicant's method to prepare his composition. Referring now to FIG. 1, in step 105 Applicant's method provides one or more parts of the jojoba plant. Such jojoba plant parts include, without limitation, seed, hulls, bark, roots, leaves, stems, and the like, but not jojoba oil. In certain embodiments, step 105 includes providing jojoba seed. In certain embodiments, jojoba seed is provided by the Desert Whale Jojoba Company of Tucson, Ariz. Jojoba seed comprises approximately 50 percent jojoba oil. The various parts of the jojoba plant, including jojoba seed, further comprises a complex mixture of jojoba oil, jojoba proteins, carbohydrates, Simmondsin, Simmondsin derivatives, and other phytochemicals. In certain embodiments, Applicant's method transitions from step 105 to step 110. In certain embodiments, Applicants' method transitions from step 105 to step 120. In certain embodiments, Applicant's method transitions from step 105 to step 130.

In step 110, Applicant presses the jojoba plant parts of step 105 to remove about 90 percent of the jojoba oil disposed in those plant parts. In certain embodiments, such mechanical pressing is performed using an expeller apparatus. The solid material remaining after removal of jojoba oil from jojoba plant parts is sometimes referred to as "jojoba meal." This jojoba meal comprises up to about 12 percent residual jojoba oil in addition to a complex mixture of jojoba proteins, sugars, Simmondsin, and other phytochemicals. In certain embodiments, Applicant's method transitions from step 110 to step 120. In certain embodiments, Applicant's method transitions from step 110 to step 130.

In step 120, the jojoba meal of step 110 is extracted using one or more non-polar compounds. By a non-polar compound, Applicant means a material having a dielectric constant of about 2 or less. Such non-polar compounds include, without limitation, pentane, hexane, cyclohexane, and the like.

In certain embodiments, step 120 further includes using super critical $CO_2$ to extract the jojoba meal. Super critical carbon dioxide comprises highly pressurized carbon dioxide. At pressures of 250 to 350 times atmospheric pressure, $CO_2$ takes on the density of a liquid and the viscosity of a gas, making it an efficient solvent. In its pressurized state, $CO_2$ is pumped into a sealed chamber containing jojoba meal, where it is allowed to circulate to remove the residual jojoba oil. Two of the major advantages of $CO_2$ are that it does not leave a chemical residue and it has a minimal to no effect on the structure of the extracted jojoba oil.

In certain embodiments, step 120 includes extracting the pressed jojoba plant parts with one or more solvents having a dielectric constant of about 6 or less. Such solvents include, without limitation, methyl formate, methyl acetate, ethyl acetate, ethers, and halogenated alkyls.

In step 130, the jojoba meal is milled. In certain embodiments, the milled jojoba meal has a average particle size of 50 microns with a standard deviation of 1.83. In certain embodiments, the milled jojoba meal has no particles larger than about 180 microns.

As those skilled in the art will appreciate, because Applicants' milled jojoba meal comprises a natural material harvested from an outdoor environment, that jojoba meal may include one or more undesirable naturally-occurring organisms, such as one or more molds and the like. In step 140, Applicant's milled jojoba meal is sterilized. In certain embodiments, Applicant's jojoba meal is irradiated to kill undesirable organisms. In certain embodiments, Applicant's jojoba meal is exposed to chemical means to kill undesirable organisms.

In certain embodiments, such chemical means include exposing said jojoba meal to one or more acids. In certain embodiments, those one or more acids include one or more hydroxy acids. In certain embodiments, such chemical means comprise one or more gaseous compounds, such as for example, ethylene oxide.

Samples of Applicant's extracted/milled jojoba meal were sent to Steris-Isomedix Services in El Paso, Tex. for sterilization with gamma rays using a Nordian Cobalt-60 Irradiator #167. TABLES 1, 2, 3, and 4, summarize the results. TABLE 1 recites the detected plate counts prior to irradiation. TABLE 2 recites the detected plate counts after irradiation with between 9 to 30 Kilograys. TABLE 3 recites the detected plate counts after irradiation with between 30 to 50 Kilograys. TABLE 4 recites the detected plate counts after irradiation with more than 50 Kilograys.

TABLE 1

| COMPONENT | ASSAY | UNITS |
|---|---|---|
| Aerobic Plate Count | 46,000 | CFU/g |
| Anaerobic Plate Count | 160 | CFU/g |
| Mold (aerophilic) | 640 | CFU/g |
| Yeast | <10 | CFU/g |

TABLE 2

| COMPONENT | ASSAY | UNITS |
|---|---|---|
| Aerobic Plate Count | 100 | CFU/g |
| Anaerobic Plate Count | <10 | CFU/g |
| Mold (aerophilic) | <10 | CFU/g |
| Yeast | <10 | CFU/g |

TABLE 3

| COMPONENT | ASSAY | UNITS |
|---|---|---|
| Aerobic Plate Count | <100 | CFU/g |
| Anaerobic Plate Count | <10 | CFU/g |
| Mold (aerophilic) | <10 | CFU/g |
| Yeast | <10 | CFU/g |

TABLE 4

| COMPONENT | ASSAY | UNITS |
|---|---|---|
| Aerobic Plate Count | <100 | CFU/g |
| Anaerobic Plate Count | <10 | CFU/g |
| Mold (aerophilic) | 10 | CFU/g |
| Yeast | <10 | CFU/g |

In certain embodiments, step 140 includes exposing the milled jojoba meal to between about 9 to about 30 Kilograys of gamma irradiation. In certain embodiments, step 140 includes exposing the milled jojoba meal to between about 30 to about 50 Kilograys of gamma irradiation. After the sterilization of step 140, milled/sterilized jojoba meal is combined with other components to form Applicant's skin whitening composition. In certain embodiments, Applicant's composition includes up to about 50 weight percent milled/sterilized jojoba meal.

In step 150, the milled/sterilized jojoba meal of step 140 is placed in a first vessel equipped with a side-scraping mixer. In certain embodiments, step 150 further includes adding water to the milled/sterilized jojoba meal. In certain embodiments, the water comprises deionized water. In step 160, one or more organic compounds comprising at least one polar group are added to that first vessel. In certain embodiments, step 160 includes adding one or more alcohols to the milled/sterilized jojoba meal of step 140. In certain embodiments such one or more alcohols include, without limitation, n-butanol, sec-butanol, tert-butanol, and the like.

In certain embodiments, step 160 includes adding one or more diols to the milled/sterilized jojoba meal of step 140. In certain embodiments such one or more diols include, without limitation, ethylene glycol, propylene glycol, polyethyleneoxide diol, polyproyleneoxide diol, and the like. In certain embodiments, step 160 includes adding one or more polyols to the milled/sterilized jojoba meal of step 140. In certain embodiments such one or more polyols include, without limitation, glycerin, polyethyleneoxide triols, polypropyleneoxide triols, and the like.

In certain embodiments, Applicant's method includes step 155 wherein one or more acids are added to the jojoba meal. In certain embodiments, the one or more acids of step 155 include, for example, formic acid, acetic acid, propionic acid, and the like. In certain embodiments, steps 150, 155, and 160, comprise mixing milled/sterilized jojoba plant parts with n-butanol and formic acid. In certain of these embodiments, an n-butanol and 1-normal formic acid mixture comprising about a 92:8 volume/volume ratio is used, and the jojoba meal/butanol/formic acid mixture is stirred for about 30 minutes.

In certain embodiments, the one or more acids of step 155 comprise one or more hydroxy-acids. By "hydroxy-acid," Applicant means a compound having a carboxylic acid functionality and a hydroxy functionality. In certain embodiments, the one or more hydroxy-acids of step 155 include one or more alpha-hydroxy acids. Such alpha-hydroxy acids include, without limitation, glycolic acid, lactic acid, mandelic acid, malic acid, citric acid, tartaric acid, and combinations thereof. In certain embodiments, the one or more acids of step 155 include one or more beta-hydroxy acids, such as and without limitation, salicylic acid, beta hydroxybutanoic acid, tropic acid, trethocanic acid, and the like, and mixtures thereof. In certain embodiments, the one or more acids of step 155 include one or more alpha hydroxy acids in combination with one or more beta-hydroxy acids.

Embodiments of Applicant's method that comprise adding one or more hydroxy acids in step 155, form compositions that have both skin whitening and skin exfoliation properties. For example, topical application of one or more alpha-hydroxy acids, and/or one or more beta-hydroxy acids, promotes dissolution of adhesions between cells in the upper layers of the skin. Such topical application of one or more hydroxy acids results in shedding dry scales from the skin, i.e. exfoliation. Such exfoliation stimulates the growth of new skin thereby providing a rejuvenated, fresher complexion.

In step 170, deionized water is placed in a second vessel. In certain embodiments Applicant's method includes step 175. In step 175, Applicant's method adds one or more water-soluble, basic compounds to the second vessel. By "water-soluble, basic compound," Applicant mean a material which when dissolved in water produces an aqueous mixture having a pH greater than 7.0. In certain embodiments, the one or more basic compounds of step 155 include NH$_4$OH, NaOH, KOH, sodium acetate, potassium acetate, sodium benzoate, potassium benzoate, and the like. In certain embodiments, the one or more basic compounds comprise polymeric materials. For example, in certain embodiments step 175 includes adding polyethyleneimine to the second vessel. In certain embodiments Applicant's method transitions from step 175 to step 180. In other embodiments, Applicant's method transitions from step 170 to step 180.

In step 180, one or more thickening agents is added to the second vessel. In certain embodiments, the one or more thickening agents of step 180 include one or more water-soluble polymers. In certain embodiments, those one or more water-soluble polymers include one or more cationic polymers. In certain embodiments, the one or more cationic polymers include guar hydroxypropyltrimonium chloride. In certain embodiments, the one or more cationic polymers include cationic hydroxyethylcellulose. In certain embodiments, the one or more cationic polymers includes salts of polyethyleneimine, polyvinylpyridine, poly-2-ethyl-2-oxazoline, and the like. In certain embodiments, the one or more cationic polymers have a charge density of between about 0.40 meq/g and about 1.2 meq/g.

In step 190, the mixture of step 160 is added to the stirred mixture of step 180 to form Applicant's composition. The composition is stirred until a uniform consistency is formed. In certain embodiments, the mixture of step 190 is stirred for at least 30 minutes.

In certain embodiments, steps 150, 155, and 160, comprise mixing milled/sterilized jojoba meal with n-butanol and formic acid, and steps 170 and 175 comprise forming an aqueous alkaline solution using, for example, NaOH, and. In these embodiments, the pH of the mixture of step 190 is initially adjusted to be about 10, and after stirring for about 30 minutes the pH is then lowered to about 7. In these embodiments, the composition of step 195 includes an aqueous component comprising dissolved Simmondsin/Simmondsin derivatives and a plurality of dissolved jojoba proteins, in combination with a heterogeneous jojoba meal component.

In certain embodiments, the Applicant's composition has a pH of about 3. In certain embodiments, the Applicant's composition has a pH of about 4. In certain embodiments, the Applicant's composition has a pH of about 5. In certain embodiments, the Applicant's composition has a pH of about 6. In certain embodiments, the Applicant's composition has a pH of about 7. In certain embodiments, the Applicant's composition has a pH between 7 and 8.

The embodiments of Applicants' method recited in FIG. 1 may be implemented separately. Moreover, in certain embodiments, individual steps recited in FIG. 1 may be combined, eliminated, or reordered. For example, certain embodiments of Applicant's method include steps 105, 130, 140, 150, 160, 170, 180, 190, and 195. Other embodiments of Applicant's method include steps 105, 120, 130, 140, 150, 160, 170, 180, 190, and 195. Other embodiments of Applicant's method includes steps 105, 110, 120, 130, 140, 150, 160, 170, 180, 190, and 195. Other embodiments of Applicant's method includes steps 105, 110, 120, 130, 140, 150, 155, 160, 170, 180, 190, and 195. Other embodiments of Applicant's method includes steps 105, 110, 120, 130, 140, 150, 160, 170, 175, 180, 190, and 195. Other embodiments of Applicant's method includes steps 105, 110, 120, 130, 140, 150, 155, 160, 170, 175, 180, 190, and 195.

Examples I and II are presented to further illustrate to persons skilled in the art how to make and use the invention and to identify certain embodiments thereof. These examples are not intended as limitations, however, upon the scope of the invention, which is defined only by the appended claims.

EXAMPLE I

The components of TABLE 5A were mixed in a first vessel. The components of TABLE 5B were mixed in a second vessel. The components of the first vessel were added to the second vessel with stirring to form one embodiment of Applicant's composition.

TABLE 5A

| COMPONENT | WEIGHT PERCENT |
|---|---|
| Deionized Water | 48 |
| Guar Hydroxypropyltrimonium Chloride* | 1 |

*Supplied by Rhodia under the tradename Jaguar C14S

TABLE 5B

| COMPONENT | WEIGHT PERCENT |
|---|---|
| Milled/Sterilized Jojoba Meal | 25 |
| Glycerin | 10 |
| Ethoxy Diglycol | 10 |
| Propylene Glycol | 5 |
| Preservative* | 1 |

*Supplied by Alzo under the tradename Phenobact, comprising a mixture of Phenoxyethanol, Methylparaben, Ethylparaben, Propylparaben, and Butylparaben.

EXAMPLE II

The components of TABLE 6A were mixed in a first vessel equipped with side scraping by first adding the water and then the jojoba meal. That mixture was stirred until uniform.

In a second vessel, the glycolic acid and lactic acid were first added to the water component with stirring. Thereafter, the sodium hydroxide was slowly added. The mixture of Table 6B was added to the first vessel with mixing. After the addition was complete, the mixture was heated to about 75° C. to about 80° C. with mixing for about ten minutes. During this ten minute period, the viscosity of the mixture increases. After holding the mixture at between about 75° C. and about 80° C. for about ten minutes, the mixture was cooled to between about 45° C. and about 50° C.

The components of TABLE 6C were mixed in a third vessel until uniform. That uniform mixture of TABLE 6C was then added to the heated, and stirred mixture formed using the components of TABLES 6A and 6B to prepare this embodiment of Applicants' composition. This embodiment of Applicant's composition was mixed until uniform and then cooled. The pH of this embodiment of Applicant's composition is between about 4 and about 4.5.

TABLE 6A

| COMPONENT | WEIGHT PERCENT |
|---|---|
| Deionized Water | 36.8 |
| Milled/Sterilized Jojoba Meal | 25 |

TABLE 6B

| COMPONENT | WEIGHT PERCENT |
|---|---|
| Deionized Water | 8 |
| Glycolic Acid (70%) | 4 |
| Lactic Acid (88%) | 1.2 |
| Sodium Hydroxide (50%) | 2.8 |

TABLE 6C

| COMPONENT | WEIGHT PERCENT |
|---|---|
| Glycerin | 8 |
| Transcutol CG | 8 |
| Propylene Glycol | 4 |
| Guar Hydroxypropyltrimonium Chloride | 1 |
| Phenobact | 1 |
| Fragrance | 0.2 |

Applicant's composition includes a plurality of jojoba proteins and amino acids. TABLE 7 recites the amino-acid composition of the extracted jojoba meal of step 120.

TABLE 7

| AMINO ACID | WEIGHT PERCENT |
|---|---|
| Lysine | 1.45 |
| Histidine | 0.61 |
| Arginine | 1.95 |
| Aspartic Acid | 2.82 |
| Threonine | 1.41 |
| Serine | 1.53 |
| Glutamic Acid | 3.36 |
| Proline | 1.44 |
| Glycine | 2.45 |
| Alanine | 1.19 |
| Valine | 1.54 |
| Methionine | 0.35 |
| Isoleucine | 1.03 |
| Leucine | 2.02 |
| Tyrosine | 1.07 |
| Phenylalanine | 1.23 |
| Cystine | 0.8 |
| Tryptophan | 0.32 |
| TOTAL | 26.57 |

Thus, Applicant's composition includes the amino acids recited in TABLE 7. In certain embodiments, Applicant's composition comprises between about 1 and about 15 weight percent amino acids.

In addition, the extracted jojoba meal of step 120 further includes Simmondsin and/or a mixture of Simmondsin derivatives and/or jojoba oil. TABLE 8 recites the reported weight percents of Simmondsin/Simmondsin derivatives and jojoba oil in other jojoba plant parts.

TABLE 8

| PLANT PART | WEIGHT PERCENT SIMMONDSIN | WEIGHT PERCENT JOJOBA OIL |
|---|---|---|
| Core wood | 0.45 | — |
| Leaves | 0.19 | 2.0 |
| Twigs | 0.63 | 1.1 |

Jaime Wisniak, The Chemistry and Technology of Jojoba Oil, America Oil Chemists' Society, at page 223.

Applicant's composition includes Simmondsin and/or a mixture of Simmondsin derivatives. In certain embodiments, the Simmondsin/Simmondsin derivative component comprises the Simmondsin/Simmondsin derivatives disposed in the jojoba plant parts of step 105 (FIG. 1). The extracted jojoba plant parts of step 120 comprise up to about 6 weight percent Simmondsin/Simmondsin derivatives. In certain embodiments, Applicant's method includes adding additional amounts of Simmondsin/Simmondsin derivatives. In certain embodiments, Applicant's composition comprises between about 0.01 weight percent and about 25 weight percent Simmondsin and/or a mixture of Simmondsin derivatives. By Simmondsin, Applicant means Compound I wherein R2 is hydrogen, R3 is OH, R4 is $OCH_3$ and R5 is $OCH_3$. By Simmondsin derivative, Applicant means Compound I wherein R2 is other than hydrogen, R3 is other than OH, R4 is other than $OCH_3$, and R5 is other than $OCH_3$.

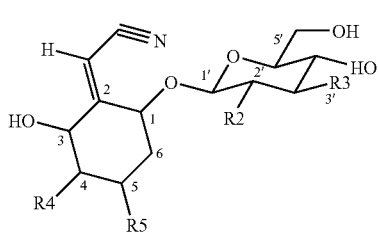

I

In certain embodiments, the R2 moiety of Compound I comprises a Ferulic acid moiety comprising compound II.

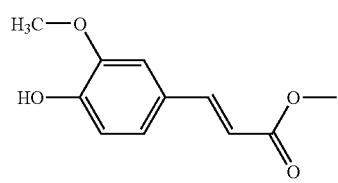

II

TABLE 9 summarizes certain embodiments of Simmondsin and/or Simmondsin derivatives that are found in Applicant's composition.

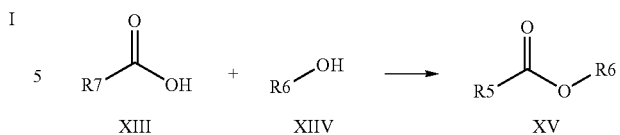

TABLE 9

| Compound | R2 | R3 | R4 | R5 | Name |
|---|---|---|---|---|---|
| III | H | OH | OCH₃ | OCH₃ | Simmondsin |
| IV | H | OH | OH | OCH₃ | 4-Demethylsimmondsin |
| V | H | OH | OCH₃ | H | 5-Demethylsimmondsin |
| VI | H | OH | OH | OH | Didemethylsimmondsin |
| VII | Compound II | OH | OCH₃ | OCH₃ | Simmondsin 2'-trans-ferulate |
| VIII | OH | Compound II | OCH₃ | OCH₃ | Simmondsin 3'-trans-ferulate |
| IX | Compound II | OH | OH | OCH₃ | 4-Demethylsimmondsin 2'-trans-ferulate |
| X | Compound II | OH | OCH₃ | OH | 5-Demethylsimmondsin 2'-trans-ferulate |
| XI | Compound II | OH | OH | OH | Didemethylsimmondsin trans-ferulate |

In certain embodiments, Applicant's composition comprises jojoba oil. In certain embodiments, the jojoba oil component comprises part or all of the residual jojoba oil in the starting pressed jojoba meal. In other embodiments, additional jojoba oil is added to Applicant's composition. Jojoba oil is obtained from the seed of the shrub *Simmondsiachinensis* which is native to the Sonoran desert. Jojoba oil is a mixture of naturally-occurring compounds obtained from the jojoba seed, sometimes called the jojoba bean. Jojoba seed contains about 50 weight percent of a yellow oil commonly referred to as jojoba oil. In contrast to other vegetable oils which comprise a mixture of triglycerides, jojoba oil comprises a mixture of long-chain esters.

As those skilled in the art will appreciate, carboxylic ester XV can be formed by the reaction of alcohol XIV and carboxylic acid XIII. In addition, an ester-group-containing compound, such as many of the constituents of jojoba oil, can be described as comprising an R5 component and an R6 component.

Jojoba oil includes a variety of ester-group-containing compounds wherein the R7 component comprises a mixture of carbon-containing moieties having, primarily, 17, 18, 20, and 22 carbon atoms, and wherein the R6 component comprises a mixture of carbon-containing moieties having, primarily, 19, 20, 22, and 24 carbon atoms. Furthermore, it is known that the R7 component of these various jojoba oil ester-group-containing constituents includes at least one carbon-carbon double bond having a cis- configuration. Sometimes such a cis- configuration is known as the Z- configuration. It is further known that the R6 component of these various jojoba oil ester-group-containing constituents includes at least one carbon-carbon double bond having a cis- configuration. Sometimes such a cis- configuration is known as the Z- configuration.

By "jojoba oil," Applicant means naturally-occurring jojoba oil and/or one or more derivatives of naturally-occurring jojoba oil. Certain derivatives of jojoba oil are known in the art. For example, isomerization of the double bond in the R7 component, and/or the R6 component, of the various jojoba esters from the cis configuration to a trans configuration yields a material that is solid at room temperature, where that solid material includes one or more crystalline compounds. U.S. Pat. No. 4,329,298 teaches a method to isomerize jojoba oil and is hereby incorporated herein by reference.

In addition, hydrogenation of the double bond in the R7 component, and/or hydrogenation of the double bond in the R6 component, of the jojoba oil ester yields a crystalline, wax-like material. Substantially fully hydrogenated jojoba oil is a solid with a melting point upwards of 70° C. As those skilled in the art will appreciate, the degree of hydrogenation can be measured using an Iodine Value ("IV"). Naturally-occurring jojoba oil has an IV of between about 80 and 85. As the percentage of carbon-carbon double bonds hydrogenated increases, the IV of that hydrogenated material decreases. As the percentage of carbon-carbon double bonds hydrogenated increases, the degree of crystallinity and the melting point of that hydrogenated material also increase.

In certain embodiments, Applicant's composition comprises between about 0.05 weight percent and about 90 weight percent jojoba oil. By jojoba oil, Applicant means a naturally-occurring mixture of ester compounds obtain from jojoba seed, isomerized jojoba oil, partially or fully hydrogenated jojoba oil, and mixtures thereof. In certain embodiments, Applicant's composition includes a plurality of particles comprising fully hydrogenated jojoba oil.

In certain embodiments, Applicant's composition further comprises a plurality of carbohydrate compounds. In certain embodiments, Applicant's composition comprises one or more monosaccharides, one or more disaccharides, and one or more complex saccharides.

In certain embodiments, Applicant's composition comprises fructose. In certain embodiments, Applicant's composition comprises fructose in a weight percentage of between about 0.50 and about 5.0. In certain embodiments, Applicant's composition comprises glucose. In certain embodiments, Applicant's composition comprises glucose in a weight percentage of between about 0.25 and about 2.5. In certain embodiments, Applicant's composition comprises sucrose. In certain embodiments Applicant's composition comprises sucrose in a weight percentage of between about 0.10 and about 1.0. In certain embodiments, Applicant's composition comprises raffinose, i.e. a trisaccharide. In certain embodiments, Applicant's composition comprises raffinose in a weight percentage of between about 0.05 and about 0.50.

In certain embodiments, Applicant's composition includes Lysine at a weight percent between about 0.01 and about 1, Histidine at a weight percent between about 0.01 and about 0.3, Arginine at a weight percent between about 0.01 and about 1, Aspartic Acid at a weight percent between about 0.05 and about 1.50, Threonine at a weight percent between about 0.01 and about 0.75, Serine at a weight percent between about 0.01 and about 0.8, Glutamic Acid at a weight percent between about 0.10 and about 1.75, Proline at a weight percent between about 0.01 and about 0.75, Glycine at a weight percent between about 0.05 and about 1.25, Alanine at a weight percent between about 0.05 and about 0.60, Valine at a weight percent between about 0.01 and about 0.77, Methionine at a weight percent between about 0.01 and about 0.25, Isoleucine at a weight percent between about 0.01 and about 0.54, Leucine at a weight percent between about 0.05 and about 1, Tyrosine at a weight percent between about 0.01 and about 0.53, Phenylalanine at a weight percent between about 0.05 and about 0.62, Cystine at a weight percent between about 0.01 and about 0.40, Tryptophan at a weight percent between about 0.01 and about 0.16, Simmondsin at a weight percent between about 0.01 and about 5, Fructose at a weight percent between about 0.01 and about 5, Glucose at a weight percent between about 0.01 and about 5, Sucrose at a weight percent between about 0.01 and about 1, and water at a weight percent between about 30 and about 98.

Pending application having Ser. No. 10/236,362, assigned to the common assignee hereof and hereby incorporated herein, describes two aqueous extracts of jojoba meal identified hereinafter as "Extract A" and "Extract B." TABLE 10 recites information generated in testing the tyrosinase activity inhibition shown by Extract A and Extract B. Extract A comprises Simmondsin/Simmondsin derivatives in an amount of about 2.36 weight percent. Extract B comprises Simmondsin/Simmondsin derivatives in an amount of about 0.44 weight percent.

Test solutions using mouse melanoma cells B16F10 were prepared, and 50 micromoles of Extract A or Extract B, along with L-DOPA at 0.025%, were added to those test solutions. The test solutions were incubated from about 1 hour to about 3 hours. The melanin content of the test solutions were measured before and after incubation using photo absorption methods. The tyrosinase activities recited in TABLE 10 were determined using those melanin values.

TABLE 10

| Concentration, v/v % | Tyrosinase Activity (%) measured using Extract A | Tyrosinase Activity (%) measured using Extract B |
| --- | --- | --- |
| 0 | 100 | 110 |
| 0.02 | 97 | 104.3 |
| 0.05 | 95.2 | 103.7 |
| 0.1 | 89.1 | 105.2 |
| 0.3 | 77.1 | 102.6 |
| 0.6 | 56 | 98.3 |
| 1.2 | 10.4 | 78.3 |
| 2.5 | −3.1 | 52.7 |

The data recited in TABLE 10, above, indicate that topical application of Applicant's composition will cause a skin whitening effect.

TABLE 11 recites information generated in testing the tyrosinase activity inhibition shown by Extract A and Extract B. Test solutions using human melanocyte cells NHEM were prepared, and 50 micromoles of Extract A or Extract B, along with L-DOPA at 0.025%, were added to those test solutions. The test solutions were incubated from about 1 hour to about 3 hours. The tyrosinase activities of the test solutions were measured before and after incubation using photo absorption methods.

TABLE 11

| Concentration, v/v % | Tyrosinase Activity (%) measured using Extract A | Tyrosinase Activity (%) measured using Extract B |
| --- | --- | --- |
| 0 | 100 | 100 |
| 0.02 | 99 | 101.2 |
| 0.05 | 94.6 | 98.3 |
| 0.1 | 92.7 | 97.8 |
| 0.3 | 78.6 | 91.8 |
| 0.6 | 56.7 | 85.7 |
| 1.2 | 39.2 | 69.4 |
| 2.5 | 1.2 | 29.5 |

The data of TABLE 11 indicate that topical application of Applicant's composition will cause a skin whitening effect.

TABLE 12 recites data relating to the melanin content of mouse B16F10 melanoma cells in the presence of various concentrations of Extract A and various concentrations of Extract B. Mouse B16F10 melanoma cells were prepared on a plate with about 2,000 cells in Dulbecco's Modified Eagle Medium with 5% v/v Fetal Bovine Serum. Those cells were cultured. A specific concentration of either Extract A or Extract B was added, and the test sample cultured for 6 days. Thereafter, the cells were washed out off the plates with Phosphate Buffer Saline Solution, and cell pellets were prepared. The color of each cell pellet was determined, and classified between 5 (black) to 1 (white) with 0 meaning not detectable. The protein content of each cell pellet was then determined, and the total melanin content in micrograms was calculated per microgram of protein. A Negative Control experiment was performed wherein no skin whitening agent was added to the cells. Positive Control experiments were performed wherein Sodium lactate was added to test cultures at either a 25 mM level or a 50 mM level.

TABLE 12

| Concentration v/v % | Negative Control | Positive Control | Extract A | Extract B |
|---|---|---|---|---|
| 0.2 | 0.543 | | 0.169 | 0.344 |
| 0.5 | 0.543 | 0.240 | 0.194 | 0.322 |
| 1.0 | 0.543 | 0.107 | 0.187 | 0.213 |

The data of TABLE 12 indicate that Applicant believes that topical application of his composition will cause a skin whitening effect.

TABLE 13 recites the observed Vidjual color determinations for the cell pellets. A Vidjual score of 5 means the cell pellet was black. A Vidjual score of 1 means the cell pellet was white. A Vidjual score of 0 means the cell pellet was not detectable, i.e. it has no color at all.

TABLE 13

| Concentration v/v % | Negative Control | Positive Control | Extract A | Extract B |
|---|---|---|---|---|
| 0.2 | 5 | | 3 | 4 |
| 0.5 | 5 | 3 | 3 | 4 |
| 1.0 | 5 | 1 | 0 | 0 |

The data of TABLE 13 indicate that topical application of Applicant's composition will cause skin whitening effects.

Applicant's extracted, milled, and irradiated, jojoba meal was tested for in vitro dermal irritancy potential using an observed ET-50 test wherein normal, human-derived epidermal keratinocytes, which closely parallel human skin, were treated with a 20% w/w mixture of Applicant's extracted/milled/irradiated jojoba meal in water. Six (6) well plates containing the dosed EpiDerm samples were incubated at 37° C., 5% $CO_2$, and greater than 90% humidity. After the appropriate exposure periods, each insert was individually removed from its plate and rinsed with a phosphate buffered saline solution to remove any residual material. Each insert was then rinsed a second time, excess liquid was shaken off, the EpiDerm sample was placed into 300 microliters of {3-[4,5-dimethylthiazol-2-yl]-2,5-diphenyl-tetrazolium bromide} ("MTT"), and the sample was then returned to the incubator.

After three hours of MTT exposure, each insert was removed and again rinsed to remove any residual MTT solution. The inserts were then placed into one well of a 24 well extraction plate. Each insert was then immersed in two milliliters of extraction solution overnight. After the exposure, a 200 microliter aliquot of each extract was removed for evaluation. A Dynatech MR 3000 Automatic Plate Reader was used to determine the absorbance of each extract at 570 nm. With the absorbance of a negative control defined as 100%, the percent absorbances of the test articles were determined. The percentage recited in TABLE 14 directly correlate with the cell metabolism in the EpiDerm samples.

TABLE 14

| EXPOSURE PERIOD | PERCENT VIABILITY | PERCENT INHIBITION |
|---|---|---|
| 1 Hour | 106 | −6 |
| 4.5 Hour | 80 | 20 |
| 20 Hour | 85 | 15 |

A semi-log scale was used to plot the percent viabilities on the linear y axis against the dosing times on the log x axis. By interpolation the time at which the percent viability would be 50%, i.e. an "ET-50" time, was estimated. Applicant's extracted, milled, irradiated, jojoba meal showed an ET-50 value greater than 24 hours. Such an ET-50 value corresponds to a "Non-Irritating" category.

In certain embodiments, Applicant's composition further includes a cosmetically acceptable carrier and/or a pharmaceutically acceptable carrier. By "cosmetically acceptable" and "pharmaceutically acceptable," Applicant means those drugs, medicaments, or inert ingredients which are suitable for use in contact with the tissues of humans and lower animals without undue toxicity, incompatibility, instability, irritation, and the like, commensurate with a reasonable benefit/risk ratio. In certain embodiments, the cosmetically acceptable vehicle will form from about 1 weight percent to about 99.9 weight percent of Applicant's composition. In certain embodiments, the cosmetically acceptable vehicle comprises between about 50 weight percent and about 99 weight percent of Applicant's composition. In certain embodiments, Applicant's composition comprises a cream, an ointment, a foam, a lotion, a plaster, or an emulsion.

One or more embodiments of Applicant's composition may be included in a wide variety of personal care products. Such personal care products include, without limitation, skin exfoliation products, skin moisturizers, massage oils, soaps, sunscreens, skin cleaners, and the like.

The present invention contemplates a method of visibly whitening human skin comprising applying to the skin a composition containing a jojoba extract wherein the composition is applied in an amount and for a period of time sufficient to visibly whiten the skin. In certain embodiments, the composition is topically applied to darkened skin areas in a predetermined or as-needed regimen either at intervals by application of a lotion or the like, it generally being the case that gradual lightening is noted with each successive application. Insofar as Applicant has determined, based upon in vitro testing, no adverse side effects will likely be encountered upon repetitive use of Applicant's composition.

While the preferred embodiments of the present invention have been illustrated in detail, it should be apparent that modifications and adaptations to those embodiments may occur to one skilled in the art without departing from the scope of the present invention as set forth in the following claims.

I claim:

1. A composition which is effective as a skin whitening and skin exfoliation agent, wherein said skin whitening composition is prepared by the steps of:
   (a) forming an aqueous mixture comprising jojoba meal;
   (b) adding one or more hydroxy acids to the mixture of part (a);
   (c) adding sodium hydroxide to the mixture of part (b);
   (d) adding one or more thickening agents to the mixture of part (c); and
   (e) mixing the mixture of part (d).

2. The composition of claim 1, wherein said one or more hydroxy acids are selected from the group consisting of one or more alpha-hydroxy acids, one or more beta-hydroxy acids, and combinations thereof.

3. The composition of claim 1, wherein said composition comprises Simmondsin.

4. The composition of claim 3, wherein said Simmondsin is selected from the group consisting of Simmondsin, 4-Demethylsimmondsin, 5-Demethylsimmondsin, Didemethylsimmondsin, Simmondsin 2'-trans-ferulate, Simmondsin 3'-trans-ferulate, 4-Demethylsimmondsin 2'-trans-ferulate, 5-Demethylsimmondsin 2'-trans-ferulate, Didemethylsimmondsin trans-ferulate, and mixtures thereof.

5. The composition of claim 3, further comprising a Ferulic acid moiety.

6. The composition of claim 1, wherein said composition comprises a plurality of amino acids.

7. The composition of claim 6, wherein said plurality of amino acids comprise:
- Lysine;
- Histidine;
- Arginine;
- Aspartic Acid;
- Threonine;
- Serine;
- Glutamic Acid;
- Proline;
- Glycine;
- Valine;
- Isoleucine;
- Leucine;
- Tyrosine;
- Phenylalanine;
- Cystine; and
- Tryptophan.

8. The composition of claim 6, further comprising one or more carbohydrates.

9. The composition of claim 8, wherein said one or more carbohydrates comprise:
- one or more monosaccharides;
- one or more disaccharides; and
- one or more trisaccharides.

10. The composition of claim 8, wherein said one or more carbohydrates comprise:
- glucose;
- fructose; and
- sucrose.

11. The composition of claim 10, further comprising raffinose.

* * * * *